US012551330B2

(12) United States Patent
Halbrecht et al.

(10) Patent No.: US 12,551,330 B2
(45) Date of Patent: Feb. 17, 2026

(54) MULTIPLANAR TENDON REALIGNMENT IMPLANTS AND RELATED SYSTEMS AND METHODS

(71) Applicant: ZKR Orthopedics, Inc., Kentfield, CA (US)

(72) Inventors: Jeffrey Halbrecht, Kentfield, CA (US); Damien Shulock, San Francisco, CA (US)

(73) Assignee: ZKR Orthopedics, Inc., Kentfield, CA (US)

( * ) Notice: Subject to any disclaimer, the term of this patent is extended or adjusted under 35 U.S.C. 154(b) by 0 days.

(21) Appl. No.: 18/817,354

(22) Filed: Aug. 28, 2024

(65) Prior Publication Data

US 2025/0073017 A1 Mar. 6, 2025

Related U.S. Application Data

(60) Provisional application No. 63/614,052, filed on Dec. 22, 2023, provisional application No. 63/579,493, filed on Aug. 29, 2023.

(51) Int. Cl.
*A61F 2/08* (2006.01)
*A61B 17/56* (2006.01)

(52) U.S. Cl.
CPC ....... *A61F 2/0811* (2013.01); *A61B 2017/564* (2013.01)

(58) Field of Classification Search
CPC ......................... A61F 2/0811; A61B 2017/564
See application file for complete search history.

(56) References Cited

U.S. PATENT DOCUMENTS 3,872,519 A 3/1975 Giannestras et al.
3,879,767 A 4/1975 Stubstad
(Continued)

FOREIGN PATENT DOCUMENTS

EP 2298179 A2 3/2011

OTHER PUBLICATIONS

Chow et al., Fracture of the tibial tubercle in the adolescent; The Journal of Bone and Joint Surgery; 72(2); pp. 231-234; Mar. 1, 1990.

(Continued)

*Primary Examiner* — Jerrah Edwards
*Assistant Examiner* — Aren Patel
(74) *Attorney, Agent, or Firm* — Fredrikson & Byron, P.A.

(57) ABSTRACT

Orthopedic implants having an implant body, a bone contact surface, and a tendon contact surface, wherein the tendon contact surface comprises an elevation ramp sloping downward from the proximal side to the distal side of the implant body and a realignment ramp sloping downward from the lateral side to the medial side of the implant body. Also disclosed are methods for repositioning a tendon that include inserting an orthopedic implant having a complex geometry tendon engagement surface between the tendon and a bone, engaging a bone engagement surface of the orthopedic implant with the bone, engaging a tendon surface with the tendon engagement surface; and causing a repositioning of the tendon via the complex geometry tendon engagement surface by at least one of (a) rotating the tendon along its axial plane, and (b) translating or shifting the tendon along its horizontal plane.

19 Claims, 11 Drawing Sheets

(56) References Cited

U.S. PATENT DOCUMENTS

| | | | |
|---|---|---|---|
| 3,886,599 | A | 6/1975 | Schlein |
| 3,889,300 | A | 6/1975 | Smith |
| 3,964,106 | A | 6/1976 | Hutter, Jr. et al. |
| 4,007,495 | A | 2/1977 | Frazier |
| 4,041,550 | A | 8/1977 | Frazier |
| 4,052,753 | A | 10/1977 | Dedo |
| 4,069,518 | A | 1/1978 | Groth, Jr. et al. |
| 4,156,944 | A | 6/1979 | Michael et al. |
| 4,158,894 | A | 6/1979 | Worrell |
| 4,164,793 | A | 8/1979 | Swanson |
| 4,285,070 | A | 8/1981 | Averill |
| 4,470,158 | A | 9/1984 | Pappas et al. |
| 4,642,122 | A | 2/1987 | Steffee |
| 4,650,490 | A | 3/1987 | Harry |
| 4,759,766 | A | 7/1988 | Buettner-Janz et al. |
| 4,904,261 | A | 2/1990 | Dove et al. |
| 4,955,915 | A | 9/1990 | Swanson |
| 5,019,104 | A | 5/1991 | Whiteside et al. |
| 5,035,700 | A | 7/1991 | Kenna |
| 5,152,790 | A | 10/1992 | Rosenberg et al. |
| 5,197,986 | A | 3/1993 | Mikhail |
| 5,231,977 | A | 8/1993 | Graston |
| 5,258,032 | A | 11/1993 | Bertin |
| 5,314,481 | A | 5/1994 | Bianco |
| 5,326,364 | A | 7/1994 | Clift, Jr. et al. |
| 5,383,937 | A | 1/1995 | Mikhail |
| 5,425,775 | A | 6/1995 | Kovacevic et al. |
| 5,480,443 | A | 1/1996 | Elias |
| 5,544,993 | A | 8/1996 | Harle |
| 5,545,229 | A | 8/1996 | Parsons et al. |
| 5,571,139 | A | 11/1996 | Jenkins, Jr. |
| 5,571,198 | A | 11/1996 | Drucker et al. |
| 5,580,353 | A | 12/1996 | Mendes et al. |
| 5,643,272 | A | 7/1997 | Haines et al. |
| 5,676,667 | A | 10/1997 | Hausman |
| 5,702,460 | A | 12/1997 | Carls et al. |
| 5,702,465 | A | 12/1997 | Burkinshaw |
| 5,702,467 | A | 12/1997 | Gabriel et al. |
| 5,733,287 | A | 3/1998 | Tepic et al. |
| 5,824,106 | A | 10/1998 | Fournol |
| 5,879,386 | A | 3/1999 | Jore |
| 5,888,203 | A | 3/1999 | Goldberg |
| 6,132,468 | A | 10/2000 | Mansmann |
| 6,143,032 | A | 11/2000 | Schafer et al. |
| 6,146,423 | A | 11/2000 | Cohen et al. |
| 6,200,347 | B1 | 3/2001 | Anderson et al. |
| 6,245,110 | B1 | 6/2001 | Grundei et al. |
| 6,280,474 | B1 | 8/2001 | Cassidy et al. |
| 6,302,915 | B1 | 10/2001 | Cooney et al. |
| 6,315,798 | B1 | 11/2001 | Ashby et al. |
| 6,368,326 | B1 | 4/2002 | Dakin et al. |
| 6,371,985 | B1 | 4/2002 | Goldberg |
| 6,409,767 | B1 | 6/2002 | Peric et al. |
| 6,468,314 | B2 | 10/2002 | Schwartz et al. |
| 6,520,964 | B2 | 2/2003 | Tallarida et al. |
| 6,527,794 | B1 | 3/2003 | Mcdevitt et al. |
| 6,579,318 | B2 | 6/2003 | Varga et al. |
| 6,589,248 | B1 | 7/2003 | Hughes |
| 6,592,622 | B1 | 7/2003 | Ferguson |
| 6,599,321 | B2 | 7/2003 | Hyde |
| 6,616,696 | B1 | 9/2003 | Merchant |
| 6,626,945 | B2 | 9/2003 | Simon et al. |
| 6,632,247 | B2 | 10/2003 | Boyer et al. |
| 6,679,914 | B1 | 1/2004 | Gabbay |
| 6,702,821 | B2 | 3/2004 | Bonutti |
| 6,709,460 | B2 | 3/2004 | Merchant |
| 6,712,856 | B1 | 3/2004 | Carignan et al. |
| 6,719,794 | B2 | 4/2004 | Gerber et al. |
| 6,800,094 | B2 | 10/2004 | Burkinshaw |
| 6,814,757 | B2 | 11/2004 | Kopylov et al. |
| 6,824,567 | B2 | 11/2004 | Tornier et al. |
| 6,852,330 | B2 | 2/2005 | Bowman et al. |
| 6,854,330 | B2 | 2/2005 | Potter |
| 6,855,150 | B1 | 2/2005 | Linehan |
| 6,866,684 | B2 | 3/2005 | Fell et al. |
| 6,890,358 | B2 | 5/2005 | Ball et al. |
| 6,893,463 | B2 | 5/2005 | Fell et al. |
| 6,896,702 | B2 | 5/2005 | Collazo |
| 6,905,513 | B1 | 6/2005 | Metzger |
| 6,911,044 | B2 | 6/2005 | Fell et al. |
| 6,916,341 | B2 | 7/2005 | Rolston |
| 6,926,739 | B1 | 8/2005 | O'Connor et al. |
| 6,966,928 | B2 | 11/2005 | Fell et al. |
| 6,974,480 | B2 | 12/2005 | Messerli et al. |
| 6,994,730 | B2 | 2/2006 | Posner |
| 7,004,971 | B2 | 2/2006 | Serhan et al. |
| 7,008,452 | B2 | 3/2006 | Hawkins |
| 7,011,687 | B2 | 3/2006 | Deffenbaugh et al. |
| 7,025,790 | B2 | 4/2006 | Parks et al. |
| 7,060,073 | B2 | 6/2006 | Frey et al. |
| 7,105,025 | B2 | 9/2006 | Castro et al. |
| 7,105,027 | B2 | 9/2006 | Lipman et al. |
| 7,124,762 | B2 | 10/2006 | Carter et al. |
| 7,160,333 | B2 | 1/2007 | Plouhar et al. |
| 7,163,563 | B2 | 1/2007 | Schwartz et al. |
| 7,182,787 | B2 | 2/2007 | Hassler et al. |
| 7,226,482 | B2 | 6/2007 | Messerli et al. |
| 7,291,169 | B2 | 11/2007 | Hodorek |
| 7,297,161 | B2 | 11/2007 | Fell |
| 7,323,012 | B1 | 1/2008 | Stone et al. |
| 7,341,602 | B2 | 3/2008 | Fell et al. |
| 7,476,225 | B2 | 1/2009 | Cole |
| 7,479,160 | B2 | 1/2009 | Branch et al. |
| 7,485,147 | B2 | 2/2009 | Pappas et al. |
| 7,500,991 | B2 | 3/2009 | Bartish, Jr. et al. |
| 7,534,270 | B2 | 5/2009 | Ball |
| 7,544,210 | B2 | 6/2009 | Schaefer et al. |
| 7,572,291 | B2 | 8/2009 | Gil et al. |
| 7,618,454 | B2 | 11/2009 | Bentley et al. |
| 7,632,311 | B2 | 12/2009 | Seedhom et al. |
| 7,637,953 | B2 | 12/2009 | Branch et al. |
| 7,641,689 | B2 | 1/2010 | Fell et al. |
| 7,722,676 | B2 | 5/2010 | Hanson et al. |
| 7,723,395 | B2 | 5/2010 | Ringeisen et al. |
| 7,726,319 | B1 | 6/2010 | Boyce |
| 7,749,276 | B2 | 7/2010 | Fitz |
| 7,758,651 | B2 | 7/2010 | Chauhan et al. |
| 7,780,670 | B2 | 8/2010 | Bonutti |
| 7,806,898 | B2 | 10/2010 | Justin et al. |
| 7,815,645 | B2 | 10/2010 | Haines |
| 7,819,918 | B2 | 10/2010 | Malaviya et al. |
| 7,875,082 | B2 | 1/2011 | Naidu |
| 7,879,105 | B2 | 2/2011 | Schmieding et al. |
| 7,896,921 | B2 | 3/2011 | Smith et al. |
| 7,896,923 | B2 | 3/2011 | Blackwell et al. |
| 7,959,675 | B2 | 6/2011 | Gately |
| 7,967,863 | B2 | 6/2011 | Frey et al. |
| 7,972,383 | B2 | 7/2011 | Goldstein et al. |
| 7,993,402 | B2 | 8/2011 | Sidler |
| 8,002,833 | B2 | 8/2011 | Fabris Monterumici et al. |
| 8,002,837 | B2 | 8/2011 | Stream et al. |
| 8,002,841 | B2 | 8/2011 | Hasselman |
| 8,034,117 | B2 | 10/2011 | Matsuzaki et al. |
| 8,043,375 | B2 | 10/2011 | Strzepa et al. |
| 8,043,380 | B1 | 10/2011 | Park et al. |
| 8,052,753 | B2 | 11/2011 | Melvin |
| 8,052,755 | B2 | 11/2011 | Naidu |
| 8,083,746 | B2 | 12/2011 | Novak |
| 8,088,168 | B2 | 1/2012 | Hassler et al. |
| 8,092,544 | B2 | 1/2012 | Wright et al. |
| 8,114,156 | B2 | 2/2012 | Hatch |
| 8,128,704 | B2 | 3/2012 | Brown et al. |
| 8,142,503 | B2 | 3/2012 | Malone |
| 8,257,444 | B2 | 9/2012 | Linares |
| 8,372,078 | B2 | 2/2013 | Collazo |
| 8,597,362 | B2 | 12/2013 | Shenoy et al. |
| 9,114,016 | B2 | 8/2015 | Shenoy et al. |
| 9,278,004 | B2 | 3/2016 | Shenoy et al. |
| 9,808,287 | B2 | 11/2017 | Halbrecht |
| 9,808,289 | B2 | 11/2017 | Ross et al. |
| 10,034,679 | B1 | 7/2018 | Boyer et al. |
| 10,918,415 | B2 | 2/2021 | Halbrecht |
| 10,918,416 | B2 | 2/2021 | Halbrecht |
| 2001/0023371 | A1 | 9/2001 | Bonutti |

(56) References Cited

U.S. PATENT DOCUMENTS

2002/0029084 A1 3/2002 Paul et al.
2002/0091447 A1 7/2002 Shimp et al.
2002/0107574 A1 8/2002 Boehm, Jr. et al.
2002/0133230 A1 9/2002 Repicci
2003/0083751 A1 5/2003 Tornier
2003/0088315 A1 5/2003 Supinski
2003/0100950 A1 5/2003 Moret
2003/0109928 A1 6/2003 Pasquet et al.
2003/0120344 A1 6/2003 Michelson
2003/0120346 A1 6/2003 Mercinek et al.
2003/0125807 A1 7/2003 Lambrecht et al.
2003/0138329 A1 7/2003 Koyano et al.
2003/0171757 A1 9/2003 Coon et al.
2003/0204265 A1 10/2003 Short et al.
2004/0039395 A1 2/2004 Coon et al.
2004/0117020 A1 6/2004 Frey et al.
2004/0133278 A1 7/2004 Marino et al.
2004/0143336 A1 7/2004 Burkinshaw
2004/0143338 A1 7/2004 Burkinshaw et al.
2004/0186585 A1 9/2004 Feiwell
2004/0215195 A1 10/2004 Shipp et al.
2004/0230303 A1 11/2004 Gomes et al.
2004/0230315 A1 11/2004 Ek
2004/0236428 A1 11/2004 Burkinshaw et al.
2004/0243240 A1 12/2004 Beaurain et al.
2005/0004671 A1 1/2005 Ross et al.
2005/0027360 A1 2/2005 Webb et al.
2005/0033424 A1 2/2005 Fell
2005/0137708 A1 6/2005 Clark
2005/0143822 A1 6/2005 Paul
2005/0222685 A1 10/2005 Hayden et al.
2005/0267584 A1 12/2005 Burdulis et al.
2005/0288788 A1 12/2005 Dougherty-Shah
2006/0036321 A1 2/2006 Henninger et al.
2006/0074423 A1 4/2006 Alleyne et al.
2006/0074492 A1 4/2006 Frey
2006/0100715 A1 5/2006 De Villiers
2006/0129243 A1 6/2006 Wong et al.
2006/0142858 A1 6/2006 Colleran et al.
2006/0161260 A1 7/2006 Thomas et al.
2006/0276907 A1 12/2006 Boyer et al.
2007/0027547 A1 2/2007 Rydell et al.
2007/0129809 A1 6/2007 Meridew et al.
2007/0173946 A1 7/2007 Bonutti
2007/0203581 A1 8/2007 Vanaclocha
2007/0208343 A1 9/2007 Magerl et al.
2007/0233141 A1 10/2007 Park et al.
2007/0265708 A1 11/2007 Brown et al.
2007/0293947 A1 12/2007 Mansmann
2007/0299528 A9 12/2007 Lotke
2008/0021566 A1 1/2008 Peters et al.
2008/0091270 A1 4/2008 Miller et al.
2008/0097617 A1 4/2008 Fellinger et al.
2008/0140094 A1 6/2008 Schwartz et al.
2008/0154267 A1 6/2008 Merchant et al.
2008/0154311 A1 6/2008 Staeubli
2008/0154371 A1 6/2008 Fell et al.
2008/0161815 A1 7/2008 Schoenefeld et al.
2008/0161933 A1 7/2008 Grotz et al.
2008/0172054 A1 7/2008 Claypool et al.
2008/0195099 A1 8/2008 Minas
2008/0234762 A1 9/2008 Forstein et al.
2008/0262618 A1 10/2008 Hermsen et al.
2008/0281422 A1 11/2008 Schmieding
2008/0281425 A1 11/2008 Thalgott et al.
2009/0012615 A1 1/2009 Fell
2009/0088763 A1 4/2009 Aram et al.
2009/0088846 A1 4/2009 Myung et al.
2009/0118830 A1 5/2009 Fell
2009/0130167 A1 5/2009 Shelton et al.
2009/0164014 A1 6/2009 Liljensten et al.
2009/0182433 A1 7/2009 Reiley et al.
2009/0198341 A1 8/2009 Choi et al.
2009/0210063 A1 8/2009 Barrett
2009/0226068 A1 9/2009 Fitz et al.
2009/0259311 A1 10/2009 Shterling et al.
2009/0259312 A1 10/2009 Shterling et al.
2009/0306783 A1 12/2009 Blum
2009/0312807 A1 12/2009 Boudreault et al.
2010/0023126 A1 1/2010 Grotz
2010/0049322 A1 2/2010 Mckay
2010/0049325 A1 2/2010 Biedermann et al.
2010/0057216 A1 3/2010 Gannoe et al.
2010/0121355 A1 5/2010 Gittings et al.
2010/0125266 A1 5/2010 Deem et al.
2010/0131069 A1 5/2010 Halbrecht
2010/0161057 A1 6/2010 Berry et al.
2010/0198354 A1 8/2010 Halbrecht
2010/0204798 A1 8/2010 Gerbec et al.
2010/0262246 A1 10/2010 Attia
2010/0292731 A1 11/2010 Gittings et al.
2010/0292733 A1 11/2010 Hendricksen et al.
2010/0305698 A1 12/2010 Metzger et al.
2011/0004305 A1 1/2011 Jansson et al.
2011/0054627 A1 3/2011 Bear
2011/0093073 A1 4/2011 Gatt et al.
2011/0172768 A1 7/2011 Cragg et al.
2011/0202138 A1 8/2011 Shenoy et al.
2011/0213466 A1 9/2011 Shenoy et al.
2011/0238180 A1 9/2011 Fritz et al.
2011/0264216 A1 10/2011 Makower et al.
2011/0270393 A1 11/2011 Marvel
2011/0288643 A1 11/2011 Linder-Ganz et al.
2012/0022649 A1 1/2012 Robinson et al.
2012/0065640 A1 3/2012 Metzger et al.
2012/0191204 A1 7/2012 Akyuz et al.
2013/0060343 A1 3/2013 Halbrecht
2013/0131802 A1 5/2013 Halbrecht
2013/0150977 A1 6/2013 Gabriel et al.
2013/0190886 A1 7/2013 Tepic et al.
2013/0304208 A1 11/2013 Clifford et al.
2014/0136154 A1 5/2014 Bojarski et al.
2014/0277444 A1 9/2014 Clifford et al.
2015/0196325 A1 7/2015 Shenoy et al.
2016/0184099 A1* 6/2016 Gotfried ............. A61F 2/30734
623/18.11
2018/0028229 A1 2/2018 Halbrecht
2018/0214261 A1 8/2018 Treacy et al.
2019/0099273 A1 4/2019 Servidio
2021/0205067 A1* 7/2021 Shulock .............. A61F 2/30749
2021/0205068 A1 7/2021 Shulock et al.
2021/0346165 A1* 11/2021 Shulock ................ A61F 2/3877

OTHER PUBLICATIONS

Gaasbeek et al.; The influence of open and closed high tibialosteotomy on dynamic patellar tracking: a biomechanical study; Knee surg. Sports Traumatol. Arthrosc.; 15(8); pp. 978-984; Aug. 1, 2007.
Maquet; Biomechanical treatment of patellofemoral osteoarthritis. Advancement of the patellar tendon: review of rheumatism and osteoarticular diseases, National Library of Medicine; vol. 30; issue 12; pp. 780-785; 1963.
Zimmer; Nex Gen trabecular metal augmentation patella, Surgical technique; 4 pages; retrieved from the internet (http://www.zimmer.com/content/ dam/zimmer-web/ documents/ en-US/pdf/ surgical•techniques/knee/NexGen-Trabecular-Metal-Augmentation-Patella•Surgical-Technique-97-7255-004-00-Rev-24-2008.pdf) on Dec. 29, 2017.
International Searching Authority, "International Search Report and Written Opinion" From Application No. PCT/US2024/044098, Mailed Jan. 8, 2025, pp. 14.

* cited by examiner

MULTIPLANAR TENDON REALIGNMENT IMPLANTS AND RELATED SYSTEMS AND METHODS

CROSS-REFERENCE TO RELATED APPLICATION(S)

This application claims the benefit under 35 U.S.C. § 119(e) to U.S. Provisional Application 63/579,493, filed Aug. 29, 2023 and entitled "Patella Tendon Multiplanar Realignment Device and Related Methods," and U.S. Provisional Application 63/614,052, filed Dec. 22, 2023 and entitled "Multiplanar Tendon Realignment Implants and Related Systems and Methods," both of which are hereby incorporated herein by reference in their entireties.

FIELD

The various embodiments herein relate to medical devices for treatment of joint pain, including, for example, implants for such treatment. More specifically, in some embodiments the implants and related methods of treatment can be used to treat knee pain caused by problems with patella-femoral joint.

BACKGROUND

Problems of the patella-femoral joint are a common cause of knee pain. The pain may arise from issues such as poor alignment of the patella (or "kneecap") or from cartilage breakdown (chondromalacia or arthritis) behind the patella or on the opposing articular surface of the femoral groove (trochlea). Conventional surgical options for treating patella-femoral pain caused by malalignment, chondromalacia or arthritis (which may include realignment of the patella, such as tilting or moving the patella, or detaching and reattaching the patellar tendon at a new location) can be very invasive and can result in prolonged recovery times.

Other options include patellar tendon realignment implants that can be positioned between the patellar tendon and tibia and have structures shaped to elevate the patellar tendon relative to the tibia, including the implant disclosed in U.S. Pat. No. 9,808,287, for example. Such an implant provides for adjustment of solely one aspect (the elevation of the tendon away from the tibia) of the relationship between the patella and the patellar tendon. That is, the implant acts solely as a ramp to adjust the position of the patellar tendon in one plane by changing the elevation of the tendon from an attachment point on the patella to the attachment point on the tibia.

There is a need in the art for improved devices and methods for addressing problems of the patella-femoral joint.

BRIEF SUMMARY

Discussed herein are various multiplanar implants, each having at least two planes on its tendon or tissue contact surface. In certain embodiments, the multiplanar contact surface can both lift the tendon or tissue away from the bone (thereby "unloading" the tendon), and realign the tendon or tissue by urging the it medially or laterally, thereby repositioning the tendon or tissue in at least two planes.

In one aspect, there is provided an orthopedic implant having an inferior portion having a tibia contact surface configured to extend over a proximal anterior portion of the tibia; a superior portion having a complex geometric tendon contacting surface configured to change a position of a patellar tendon by one or a combination of (a) rotating the patellar tendon along its axial plane; (b) tilting the patella along its coronal plane or (c) translating or shifting the patellar tendon along it horizontal plane when the curved surface of the first portion is engaged with the tibia; and a fixation mechanism adapted to attach the orthopedic implant to the tibia. In an additional aspect, the tibia contact surface comprising three feet arranged to support the implant when in use and attached to the tibia. In still another aspect, the tibia contact surface comprising two feet arranged in cooperation with an edge to support the implant when in use and attached to the tibia.

In an alternative aspect, there is provided a method for repositioning a patellar tendon by inserting an orthopedic implant having a complex geometry tendon engagement surface between the patellar tendon and a tibia; engaging a tibia engagement surface of an inferior portion of the orthopedic implant with the tibia; engaging a patellar tendon surface with the complex geometry tendon engagement surface; and inducing one or more of (a) rotating the patellar tendon along its axial plane; (b) tilting the patella along its coronal plane or (c) translating or shifting the patellar tendon along it horizontal plane so as to make a desired realignment of the patellar tendon. In one alternative, the step of engaging a tibia engagement surface further comprises adjusting the position of the implant for support by three feet positioned in a spaced apart arrangement on the inferior portion of the implant. In another alternative, there is a step of engaging a tibia engagement surface further comprises adjusting the position of the implant for support by two feet positioned in a spaced apart arrangement from an articulating surface on the inferior portion of the implant.

In Example 1, an orthopedic implant comprises an implant body comprising a top side, a bottom side, a distal side, a proximal side, a medial side, and a lateral side, a bone contact surface disposed on the bottom side, the bone contact surface configured to be contactable with a bone, and a tendon contact surface disposed on the top side. The tendon contact surface comprises an elevation ramp sloping downward from the proximal side to the distal side of the implant body and a realignment ramp sloping downward from the lateral side to the medial side of the implant body.

Example 2 relates to the orthopedic implant according to Example 1, wherein the tendon contact surface is configured to change a position of a tendon by at least one of (a) rotating the tendon along its axial plane, and (b) translating or shifting the tendon along its horizontal plane when the bone contact surface is engaged with the bone.

Example 3 relates to the orthopedic implant according to Example 1, wherein the elevation ramp slopes downward from the proximal side to the distal side of the implant body at an angle of from about 5 degrees to about 35 degrees.

Example 4 relates to the orthopedic implant according to Example 1, wherein the realignment ramp slopes downward from the lateral side to the medial side of the implant body at an angle of from about 5 degrees to about 30 degrees.

Example 5 relates to the orthopedic implant according to Example 1, wherein the bone contact surface comprises at least two feet arranged to support the implant while attached to the bone.

Example 6 relates to the orthopedic implant according to Example 1, wherein the bone contact surface comprises two feet arranged in cooperation with an articulating surface to support the implant while attached to the bone.

Example 7 relates to the orthopedic implant according to Example 1, further comprising a fixation mechanism associated with the implant body, wherein the fixation mechanism is configured to attach the implant body to the bone.

Example 8 relates to the orthopedic implant according to Example 7, wherein the fixation mechanism comprises at least two openings defined through the implant body, and at least two fixation screws, wherein each of the at least fixation screws is configured to be positionable through one of the at least two openings.

Example 9 relates to the orthopedic implant according to Example 1, wherein the bone is a tibia, and wherein the tendon is a patellar tendon.

In Example 10, an orthopedic implant comprises an implant body comprising a top side, a bottom side, a distal side, a proximal side, a medial side, and a lateral side, a tibia contact surface disposed on the bottom side, the tibia contact surface configured to be contactable with a tibia, and a tendon contact surface disposed on the top side. The tendon contact surface comprises an elevation ramp sloping downward from the proximal side to the distal side of the implant body, and a realignment ramp sloping downward from the lateral side to the medial side of the implant body, wherein the tendon contact surface is configured to change a position of a patellar tendon by at least one of (a) rotating the patellar tendon along its axial plane, and (b) translating or shifting the patellar tendon along its horizontal plane when the tibia contact surface is engaged with the tibia.

Example 11 relates to the orthopedic implant according to Example 10, wherein the changing the position of the patellar tendon further results in tilting a patella coupled to the patellar tendon along its coronal plane.

Example 12 relates to the orthopedic implant according to Example 10, wherein the elevation ramp slopes downward from the proximal side to the distal side of the implant body at an angle of from about 5 degrees to about 35 degrees.

Example 13 relates to the orthopedic implant according to Example 10, wherein the realignment ramp slopes downward from the lateral side to the medial side of the implant body at an angle of from about 5 degrees to about 30 degrees.

Example 14 relates to the orthopedic implant according to Example 10, wherein the tibia contact surface comprises two feet arranged in cooperation with an articulating surface to support the implant while attached to the tibia.

Example 15 relates to the orthopedic implant according to Example 10, further comprising a fixation mechanism associated with the implant body, wherein the fixation mechanism is configured to attach the implant body to the tibia.

In Example 16, a method for repositioning a patellar tendon comprises inserting an orthopedic implant having a complex geometry tendon engagement surface between the patellar tendon and a tibia, engaging a tibia engagement surface of the orthopedic implant with the tibia, engaging a patellar tendon surface with the complex geometry tendon engagement surface, and causing a repositioning of the patellar tendon via the complex geometry tendon engagement surface by at least one of (a) rotating the patellar tendon along its axial plane, and (b) translating or shifting the patellar tendon along its horizontal plane.

Example 17 relates to the method according to Example 16, wherein the repositioning of the patellar tendon further causes tilting a patella coupled to the patellar tendon along its coronal plane.

Example 18 relates to the method according to Example 16, wherein the step of engaging a tibia engagement surface further comprises adjusting the position of the implant for support by three projections positioned in a spaced apart arrangement on the inferior portion of the implant.

Example 19 relates to the method according to Example 17, wherein the three projections comprising two feet and an articulating surface.

Example 20 relates to the method according to Example 16, further comprising attaching the orthopedic implant to the tibia after engaging the tibia engagement surface with the tibia.

All of the methods and apparatuses described herein, in any combination, are herein contemplated and can be used to achieve the benefits as described herein. While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

The various embodiments described herein relate to multiplanar realignment devices and related methods for treatment of various joint conditions, such as, for example, patellofemoral cartilage degeneration ("PCD," i.e., degeneration of cartilage in the patellofemoral compartment), patellofemoral pain, chondromalacia, and/or patella instability by creating forces to act against or induce a desired realignment in the position of either or both of the patellar tendon and the patella in at least two planes. These device implementations provide for more complex realignments/adjustments of the patellar tendon and/or the patella in comparison to known devices. In contrast, the known realignment devices are essentially ramps that operate solely to lift the patellar tendon away from the tibia and thereby change the slope of the patellar tendon in a single plane from an attachment point on the patella to the attachment point on the tibia. The implementations herein can be implanted between a patient's tibia and patellar tendon to not only lift the tendon away from the tibia (thereby "unloading" the tendon), but also to realign the tendon by urging the tendon medially or laterally, thereby repositioning the tendon in at least two planes. Further, the various embodiments herein can also rotate the patellar tendon around its longitudinal axis, thereby resulting in a "tilting" of the tendon and creating a realignment in a third plane (the "axial plane"). In addition, this realignment of the patellar tendon also results in realignment of the patella as well, as will be described in further detail below. These multiple plane realignment implants and methods as disclosed or contemplated herein offer a minimally-invasive surgical alternative for patients who fail conservative care and can replace invasive surgeries with long recovery times (e.g., tibial tubercle osteotomy) or invasive and irreversible surgeries (knee replacement).

Embodiments of the patellar multiplanar implant and related methods described herein can be used for realigning the patellar tendon and, in certain cases, the patella and unloading degenerated cartilage in the patellofemoral compartment. The realignment of the patella can improve the stability of the patella by adjusting the tracking of the patella in the trochlear groove. Thus, the implant can act to unload and realign the patella to address problems related to patella cartilage degeneration as well as to address problems of patella instability. In various embodiments as will be described in additional detail below, unloading and realigning is achieved by adjusting the position of a patellar tendon by one or a combination of (a) rotating the patellar tendon along its axial plane; (b) tilting the patella along its coronal plane or (c) translating or shifting the patellar tendon along its horizontal plane.

Figure 1A:
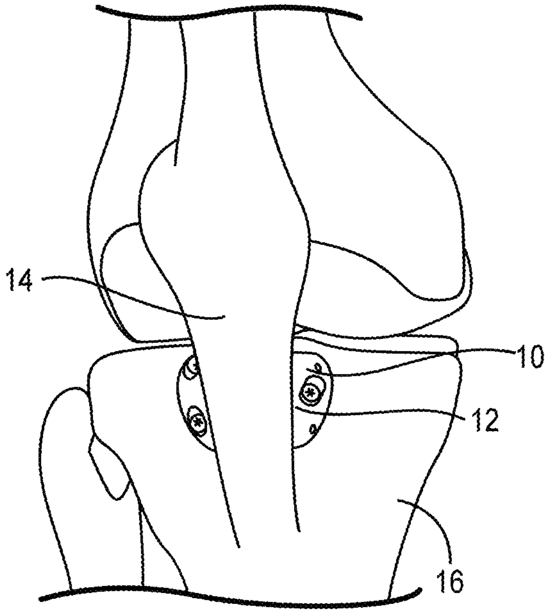
FIG. 1A is a front view of a patient's right knee with a multiplanar implant attached thereto, according to one embodiment.
Figure 1B:
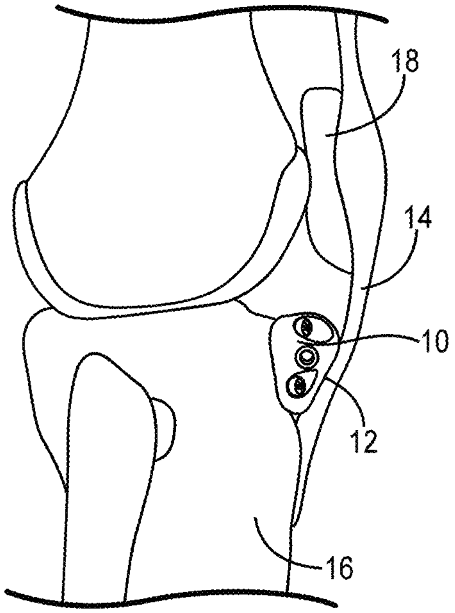
FIG. 1B is a side view of the implant of FIG. 1A from the lateral side of the knee, according to one embodiment.
Figure 1C:
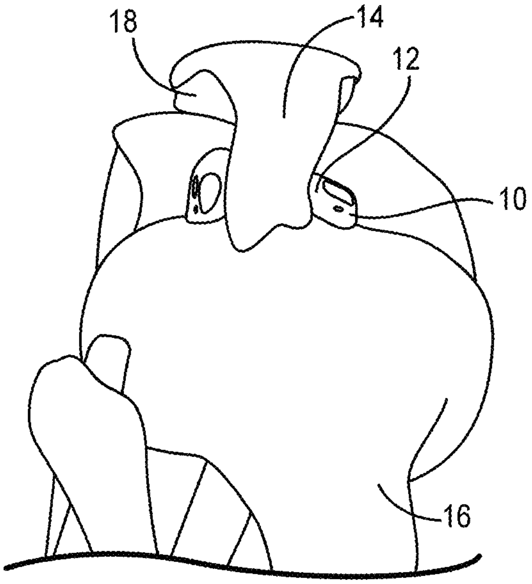
FIG. 1C is a view of the implant of FIG. 1A from below the knee, according to one embodiment.

One exemplary image of a multiplanar patellar implant 10 implanted in the right knee of a patient is depicted in FIGS. 1A-1C. More specifically, FIG. 1A depicts a front view of the patient's right knee with the implant 10 disposed between the patellar tendon 14 and the tibia 16 such that the implant 10 is "under" the tendon 14 and attached to the tibia 16. Further, FIG. 1B provides a side view of the patient's right knee and the implant 10 (viewed from the lateral side of the knee), while FIG. 1C provides a bottom view of the knee and the implant 10 as shown from the viewpoint of the patient's right foot. The implant 10 has a tendon contact surface 12 that causes the tendon 12, and in some cases, the patella 18, to be realigned as desired and as described in additional detail below.

Figure 2A:
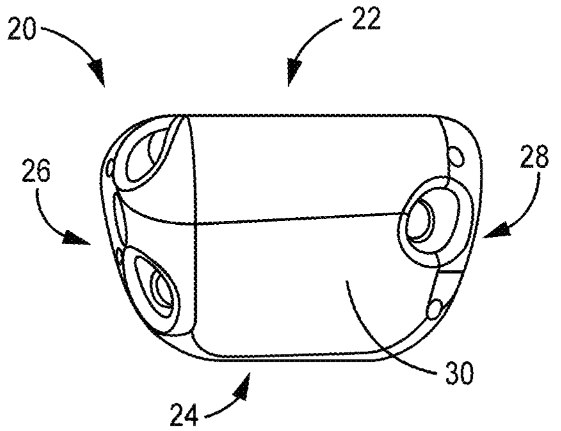
FIG. 2A is a top of a multiplanar implant, according to one embodiment.
Figure 2B:
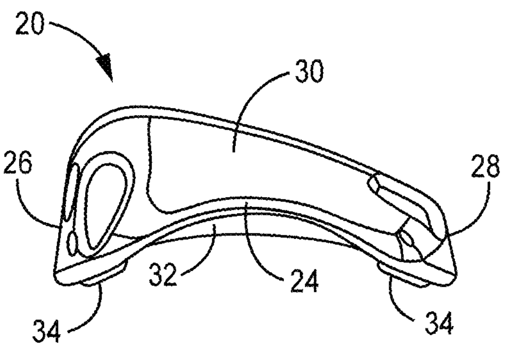
FIG. 2B is a side view (from the distal side) of the implant of FIG. 2A, according to one embodiment.
Figure 2C:
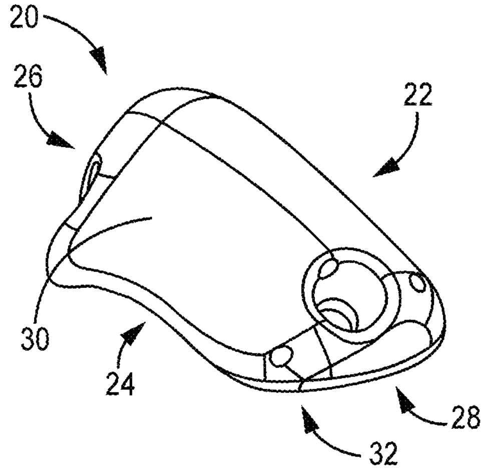
FIG. 2C is a perspective view of the implant of FIG. 2A, according to one embodiment.
Figure 2D:
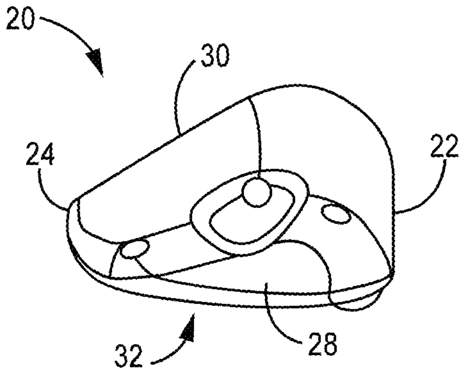
FIG. 2D is a side view (from the medial side) of the implant of FIG. 2A, according to one embodiment.
Figure 2E:
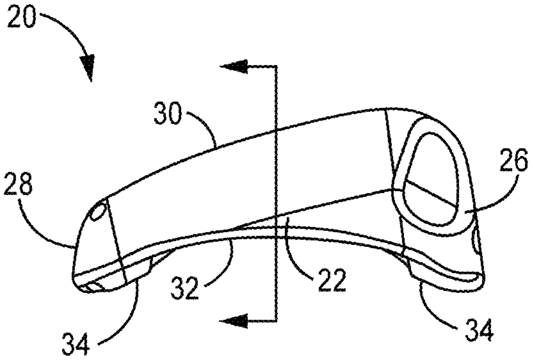
FIG. 2E is a side view (from the proximal side) of the implant of FIG. 2A, according to one embodiment.
Figure 2F:
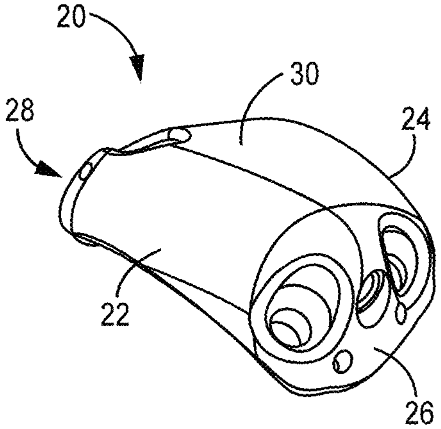
FIG. 2F is a different perspective view of the implant of FIG. 2A, according to one embodiment.
Figure 2G:
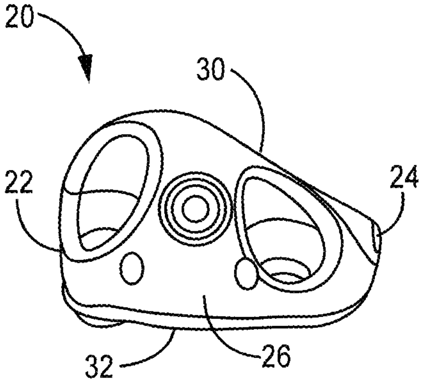
FIG. 2G is a side view (from the lateral side) of the implant of FIG. 2A, according to one embodiment.
Figure 2H:
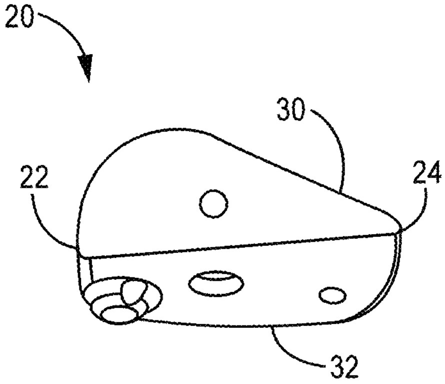
FIG. 2H is a cross-sectional view of the portion of the implant of FIG. 2A identified by the line in FIG. 2E, according to one embodiment.
Figure 2I:
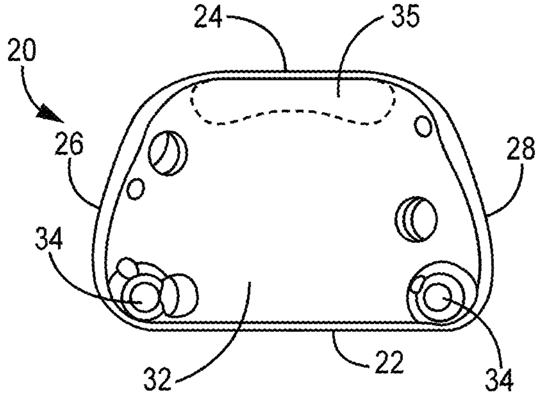
FIG. 2I is a bottom view of the implant of FIG. 2A, according to one embodiment.

One specific multiplanar patellar implant 20 for use in a patient's right knee is shown in detail in FIGS. 2A-2I, according to one embodiment. FIG. 2A is a top view, FIG. 2B is a side view (viewed from the distal side), FIG. 2C is a perspective view, FIG. 2D is a side view (viewed from the medial side), FIG. 2E is a side view (view from the proximal side), FIG. 2F is a perspective view, FIG. 2G is a side view (viewed from the lateral side), FIG. 2H is a cross-sectional view of the portion of the implant 20 identified by the line in FIG. 2E), and FIG. 2I is a bottom view of the device 20. It is noted that, for ease of understanding, all of the implant embodiments depicted and discussed herein are intended for implantation in a patient's right knee. It is understood that the left knee implants are substantially similar to the various right knee implants herein, except that they are mirror images thereof.

As shown in FIGS. 2A-I, the implant 20 has a proximal side 22, a distal side 24, a lateral side 26, and a medial side 28. For purposes of this application, the sides of the implant 20 are identified based on the intended positioning of the implant 20 when attached to the patient's right tibia, with the proximal side 22 facing proximally toward the patient's right knee joint, the distal side 24 facing toward the patent's right foot, the lateral side 26 facing toward the lateral side of the patient's right leg (away from the left leg), and the medial side 28 facing toward the medial side of the patient's right leg (toward the left leg). However, the names of the sides are provided solely for convenience and ease of understanding and are not limiting. In alternative descriptions, the proximal side 22 can be a first side 22, the distal side 24 can be a second side 24, the lateral side 26 can be a third side 26, and the medial side 28 can be a fourth side 28.

The implant 20 also has a top (or "contact") surface 30 that is a multiplanar surface 30 and is in contact with the patellar tendon when the implant 20 is disposed between the tibia and the patellar tendon (in a fashion similar to that depicted in FIG. 1 above). Further, the implant 20 has an underside (or "bottom surface") 32 that faces toward the tibia and can be in contact with the tibia when the implant 20 is attached to the tibia.

In addition, in certain embodiments, the device 20 can have two contact projections (or "feet") 34 on the bottom surface 32 that are protruding structures such as posts or stubs. In addition, the bottom surface 32 also has a contact area 35 at or near the distal side 24 of the implant 20. The two contact projections 34 along with the contact area 35 facilitate contact with the tibia during implantation and help maintain stability of the implant 20 on the tibia surface (in a fashion similar to a three-legged stool) once it is attached to the tibia. In a further alternative, the two feet 34 can be adjustable such that the bottom surface 32 can be tailored to the unique contours of an individual patient's tibia, thereby optimizing the stability of the implant 20 for that specific patient. In additional alternative implementations, the implant can have one, three, four, five, six, or any number of projections similar to the feet 34 as shown, including some embodiments in which one or more projections are located in or near the contact area 35.

In one specific implementation, the implant 20 is made of polyether ether ketone ("PEEK"). Alternatively, the implant 20 can be made of any combination of one or more other polymeric materials, one or more metals, one or more reabsorbable materials, or any other materials that provide the same structural qualities as PEEK.

According to some implementations, the device 20 can have a length (from the proximal side 22 to the distal side 24) ranging from about 12 mm to about 25 mm. Alternatively, the device 20 can have a length ranging from about 21 mm to about 25 mm. In a further alternative, a set of devices 20 of different sizes can be provided to allow for use of the appropriate size for each patient. As such, a small device 20 might have a length of 21 mm, a medium device 20 might have a length of 23 mm, and a large device 20 might have a length of 25 mm. In a further alternative, the length can be any known length as need to provide the best and most stable fit for the device 20.

In accordance with certain embodiments, the device 20 can have a height (the distance from the contact surface 30 to the bottom surface 32) ranging from about 5 mm to about 20 mm. Alternatively, the device 20 can have a height ranging from about 8 mm to about 12 mm. In a further alternative, a set of devices 20 of different sizes can be provided as mentioned above such that a small device 20 might have a height of 8 mm, a medium device 20 might have a height of 10 mm, and a large device 20 might have a height of 12 mm. In a further alternative, the height can be any known height as needed to provide the desired amount of elevation for the patellar tendon and/or to realign the tendon as desired, as discussed in additional detail elsewhere herein. It is noted that the height as discussed in this paragraph is equivalent to the "peak height" as discussed below.

Figure 3A:
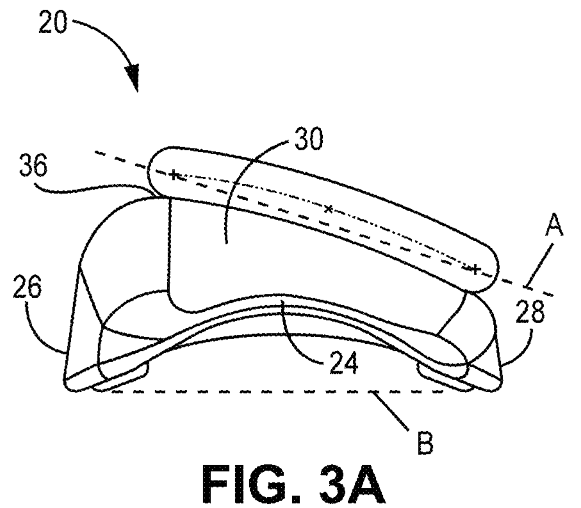
FIG. 3A is a side view (from the distal side) of a multiplanar implant highlighting a first plane of the contact surface, according to one embodiment.
Figure 3B:
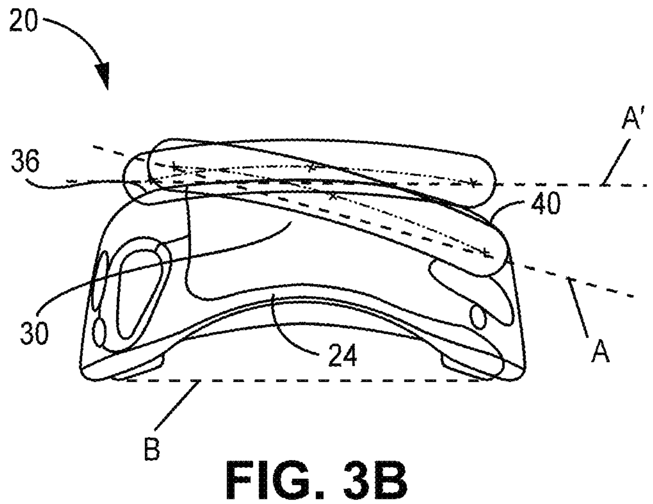
FIG. 3B is the same side view of the implant of FIG. 3A overlaid with the corresponding side of a known "neutral" implant to highlight the difference in the position of the first plane of the contact surface of the implant of 3A in comparison to the first plane of the contact surface of the neutral implant, according to one embodiment.
Figure 3C:
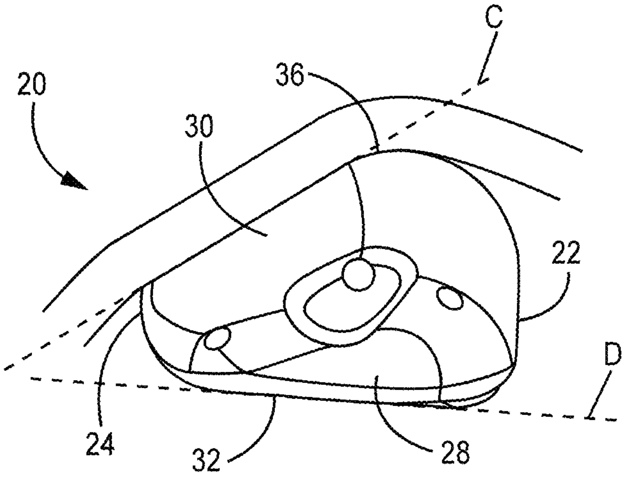
FIG. 3C is a side view (from the medial side) of the implant of FIG. 3A highlighting a second plane of the contact surface, according to one embodiment.

It is the configuration and complex geometry of the contact surface (such as contact surface 30 above) of the various implant implementations herein that allows the device to realign the patellar tendon and, in some cases, the patella. More specifically, as best shown in FIGS. 3A-3C according to one embodiment, the contact surface 30 is disposed at two different angles in two different planes. As shown in FIG. 3A, the plane of the contact surface 30 extending from the lateral side 26 to the medial side 28 (the "horizontal plane" as represented by line A, which will also be referred to as the "realignment plane" or "realignment ramp") is disposed at an angle of about 16 degrees in relation to a plane extending between the outermost portions of the two feet 34 as represented by the line B. It is understood that plane B represents a 0° horizontal plane of the implant 20 that is equivalent to a cross-sectional plane that is disposed through the center of implant 20 and further is parallel to the plane of any surface on which the implant 20 is positioned. In other words, the lateral-to-medial slope or realignment ramp represented by line A has an angle of about 16 degrees in relation to the plane B (and thus in relation to the surface on which the implant 20 is positioned. Alternatively, the horizontal plane A (the lateral-to medial slope) can be disposed at an angle in relation to plane B ranging from about 5 degrees to about 30 degrees. In a further alternative, the horizontal plane A can be disposed at an angle ranging from about 1 degree to about 45 degrees. In yet another alternative, the angle can be any known angle as needed to achieve the desired amount of realignment of the patellar tendon as discussed in additional detail elsewhere herein. As such, the height of the implant 20 (the distance from the contact surface 30 to the bottom surface 32) is greater at the peak height 36 of the contact surface 30 along plane A (near the lateral side 26) in comparison to the height of the contact surface 30 at the medial side 28 by an amount resulting in the desired realignment ramp (or horizontal plane or lateral-to-medial slope A). For example, in one embodiment, the peak height 36 is about 20 mm (as discussed above), while the height at the medial side 28 is about 6 mm. Alternatively, as discussed above, the peak height 36 can range from about 5 mm to about 20 mm, while the height at the medial side 28 can range from about 4 mm to about 10 mm.

In one specific, non-limiting example in FIG. 3B, one embodiment of the multiplanar implant 20 is depicted in an overlay with a known "neutral" implant 40 disposed behind the multiplanar implant 20 such that the difference in the horizontal planes A, A' of the two devices 20, 40 can be easily seen. The known neutral implant 40 as shown represents a known device that is not multiplanar—such as, for example, a version of the device disclosed in U.S. Pat. No. 9,808,287, which is mentioned above. That is, the known neutral implant has a horizontal plane A' that is substantially parallel with plane B as shown. In contrast, the multiplanar tendon realignment implant 20 has a realignment ramp or horizontal plane A disposed at an angle of about 16 degrees in relation to the horizontal plane A' of the neutral implant 40. Alternatively, the realignment ramp of the multiplanar implant 20 can be disposed at an angle ranging from about 5 to about 30 degrees in relation to horizontal plane A' of known implant 40.

In addition, as shown in FIG. 3C, the various multiplanar tendon realignment implant implementations disclosed or contemplated herein—such as the implant 20 as shown—also have an angled second plane. More specifically, the plane of the contact surface 30 extending from the proximal side 22 to the distal side 24 (the "elevation plane" as represented by line C, which will also be referred to as the "elevation ramp") is disposed at an angle of about 30 degrees in relation to a plane extending along the bottom surface 32 as represented by the line D. It is understood that plane D, much like plane B as discussed above, represents a 0° horizontal plane of the implant 20 that is equivalent to a cross-sectional plane that is disposed through the center of implant 20 and further is parallel to the plane of any surface on which the implant 20 is positioned. Alternatively, the elevation plane C can be disposed at an angle in relation to plane D ranging from about 5 degrees to about 35 degrees. In a further alternative, the elevation plane C can be disposed at an angle ranging from about 1 degree to about 45 degrees. In yet another alternative, the angle can be any known angle as needed to achieve the desired amount of elevation of the patellar tendon as discussed in additional detail elsewhere herein. As such, the height of the implant 20 (the distance from the contact surface 30 to the bottom surface 32) is greater at the peak height 36 near the proximal side 22 in comparison to the height at the distal side 24 by an amount resulting in the elevation ramp or elevation plane C. For example, in one embodiment, the peak height 36 near the proximal side 22 is about 12 mm, while the height at the distal side 24 is about 1 mm. Alternatively, the peak height 36 near the proximal side 22 can range from about 6 mm to about 20 mm, while the height at the distal side 24 can range from about 0 mm to about 2 mm.

Figure 4A:
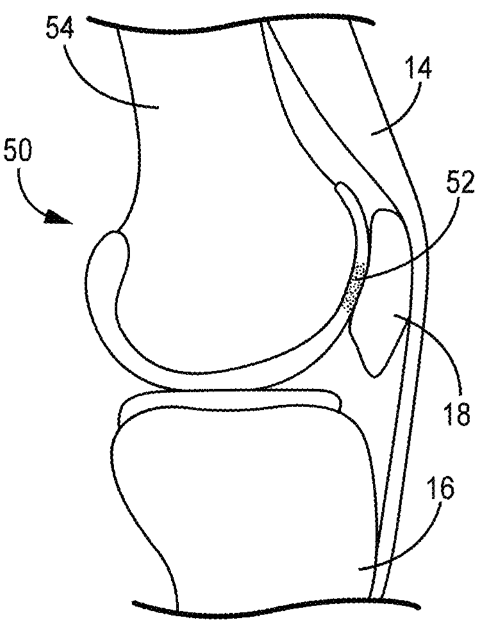
FIG. 4A is a side view of a patient's right knee from the lateral side of the knee with no implant.
Figure 4B:
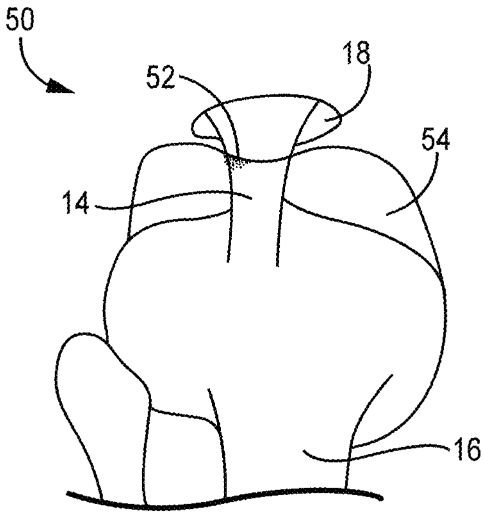
FIG. 4B is a view of the right knee of FIG. 4A from below the knee.
Figure 5A:
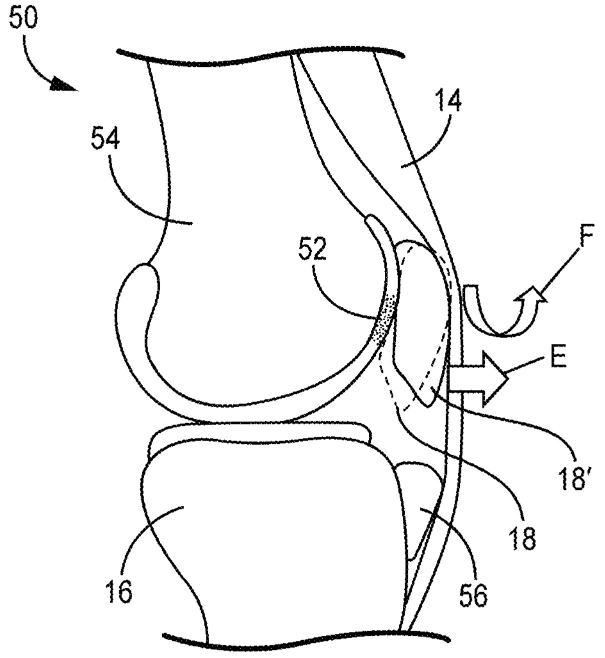
FIG. 5A is a side view of a patient's right knee from the lateral side of the knee with a multiplanar implant attached thereto, according to one embodiment.
Figure 5B:
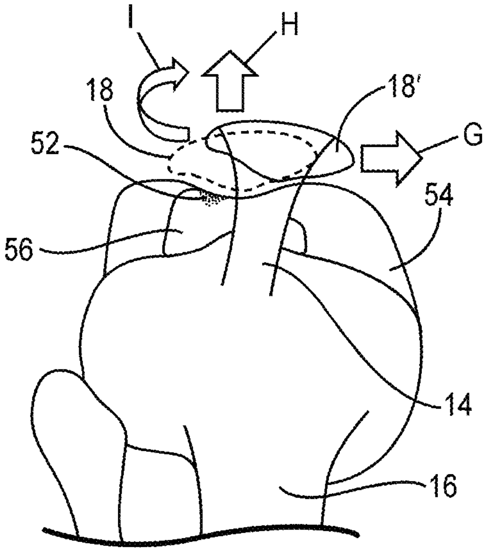
FIG. 5B is a view of the implant of FIG. 5A from below the knee, according to one embodiment.

It is the existence of the at least two angled planes or ramps on the contact surface 30 of the implant 20 as discussed above that makes it possible to realign the patellar tendon and/or the patella as mentioned above. More specifically, in one exemplary implementation as shown in FIGS. 4A-5B, the multiplanar contact surface 30 can realign the patellar tendon 14 and the patella 18 in the following fashion. An exemplary right knee 50 exhibiting patella-femoral joint pain (as represented by the darker spot 52 in the knee) is depicted in FIGS. 4A and 4B. In contrast, FIGS. 5A and 5B depict the same knee 50 after a multiplanar tendon realignment implant 56 has been attached to the tibia 16 as shown. The implant 56 can be any of the implant embodiments disclosed or contemplated herein. Once the implant 56 is implanted as shown, it can be seen that both the patellar tendon 14 and the patella 18 are repositioned in multiple planes as a result.

More specifically, a comparison of FIGS. 4A and 5A show that the patella 18 has been realigned from its original position (as shown in FIG. 4A and via the dotted lines in FIG. 5A) into a new, realigned (or "tilted") position 18' (as shown in FIG. 5A) in which the realigned patella 18' has been both (1) urged anteriorly (as shown via arrow E) and (2) rotated or "tilted" (as shown via arrow F) away from the damaged/painful area 52 in the knee 50. Further, a comparison of FIGS. 4B and 5B show that the patella 18 has also been (1) shifted medially (as shown via arrow G) and (2) elevated (urged away from the femur 54) as shown via arrow H, and (3) rotated axially in a clockwise direction (as shown via arrow I) from its original position 18 (as shown in FIG. 4B and via the dotted lines in FIG. 5B) into a new shifted and elevated position 18" away from the damaged/painful area 52 as shown in FIG. 5B.

Similarly, a comparison of FIGS. 4A and 5A show that the patellar tendon 14 has been elevated from its original position (as shown in FIG. 4A) in relation to the tibia 16 into an "elevated" position in which the tendon 14 has been urged away from (or "elevated in relation to") the tibia 14 (as shown in FIG. 5A). Further, a comparison of FIGS. 4B and 5B show that the patellar tendon 14 has also been shifted medially from its original position (as shown in FIG. 4B) into a new, realigned horizontal position in the medial direction as shown in FIG. 5B.

As such, each of the various implant embodiments herein has a complex, multiplanar geometry on its contact surface—including at least an elevation ramp and a realignment ramp—that can divert or realign the path of the patellar tendon and, in some cases, can realign the patella as well. More specifically, the new, realigned path of the patellar tendon causes the realignment of the patella while "unloading" the patellofemoral joint. As a result, the elevation plane or ramp C as discussed above defines the amount of anterior lift that the tendon experiences in relation to the tibia. According to various implementations, the ramp can be continuous, straight, and can have a generous radius at the proximal end to minimize trauma to the tendon. Further, the realignment plane or ramp A as discussed above establishes the distance that the patellar tendon is shifted horizontally, thereby unloading the side of the joint away from which the tendon is shifted. As a result, the various implant embodiments herein can serve to mimic the benefits of a tibial tubercle osteotomy by similarly realigning the patella and unloading the patellofemoral cartilage while avoiding the invasive nature of the procedure.

Without being limited by theory, it is believed that the complex geometry (the two ramps as described herein) of the contact surface of the various embodiments herein provide tendon realignment by creating an advantageous combination of force vectors. That is, as described in detail herein, the contact surface induces force vectors that can (a) rotate the patellar tendon along its axial plane, (b) tilt the patella along its coronal plane, and/or (c) translate (shift) the tendon along its horizontal plane, alone or in any combination.

All of the implant embodiments depicted and discussed herein have a realignment ramp A in which the contact surface has a greater height at or near the lateral side and a lesser height at or near the medial side, thereby urging the patellar tendon toward the medial side of the patient's knee. One reason that all of the implementations discussed herein have a ramp A with a higher lateral side is because in most patients, the cartilage damage in the patella femoral joint is on the lateral side of the joint. However, it is important to note that, for those patients in which the damage is located on the medial side of the joint, alternative implant embodiments are contemplated herein that can have a contact surface with a realignment ramp urging the tendon in the opposite direction—toward the lateral side of the knee. It is understood that these alternative embodiments are substantially similar to the embodiments discussed in detail herein except that the configuration has the necessary structure to accomplish the realignment of the tendon and patella in the opposite directions of those discussed above. Thus, certain implementations of the implant can have a realignment ramp A in which the contact surface has a greater height at or near the medial side and a lesser height at or near the lateral side, thereby urging the patellar tendon toward the lateral side of the patient's knee. In such embodiments, all the other components, structures, and/or features of the implant remain substantially the same as the specific implants depicted in the figures and discussed in detail above.

Figure 6A:
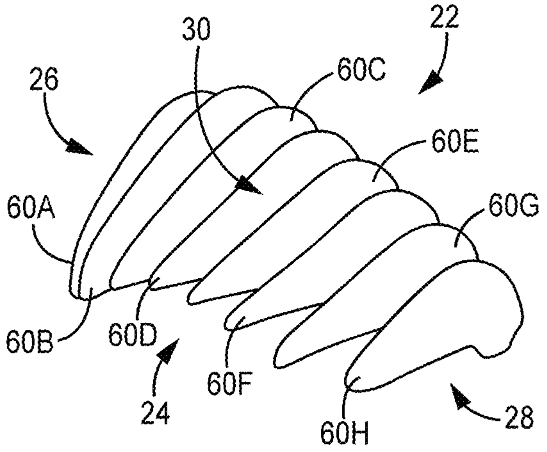
FIG. 6A is a perspective view of schematic "slices" of a multiplanar implant in which each slice is a cross-sectional section that extends from the proximal side to the distal side, according to one embodiment.
Figure 6B:
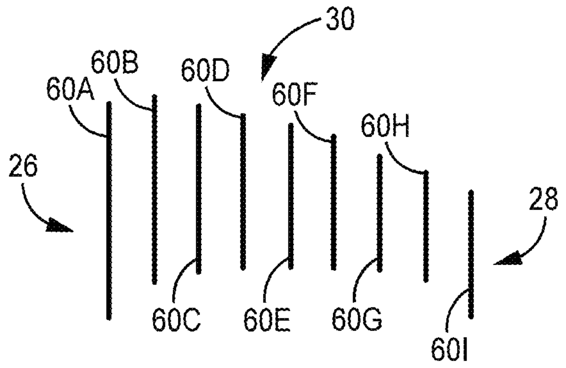
FIG. 6B is a side view (from the distal side) of the slices of the implant of FIG. 6A, according to one embodiment.
Figure 7:
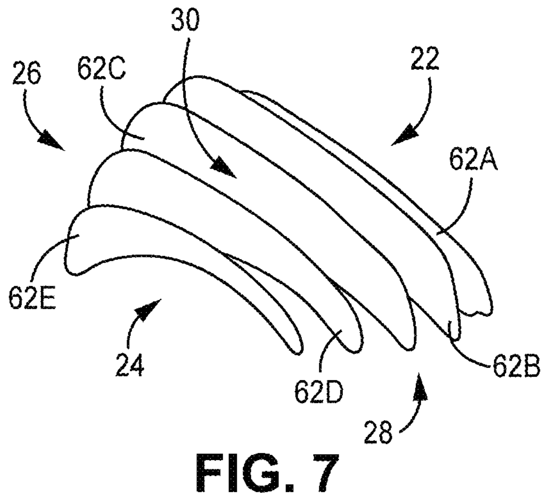
FIG. 7 is a perspective view of schematic "slices" of a multiplanar implant in which each slice is a cross-sectional section that extends from the lateral side to the medial side, according to one embodiment.
Figure 6C:
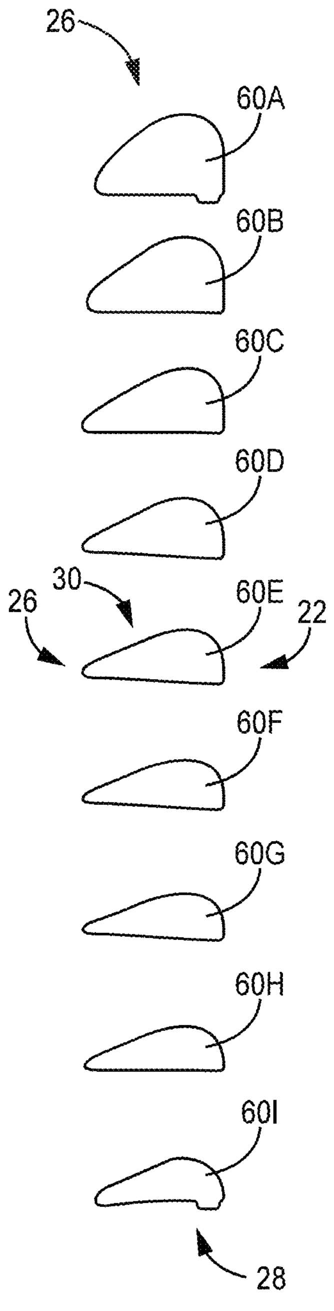
FIG. 6C is a front view of each of the slices of the implant of FIG. 6A, according to one embodiment.

Returning now to the right knee multiplanar implant embodiment 20 as discussed in detail above, the specific dimensions of one exemplary implementation will be discussed in additional detail with respect to FIGS. 6A-7. More specifically, FIGS. 6A-7 depict one embodiment of the multiplanar implant 20 (similar to the implant 20 as shown in FIGS. 2A-2I) in which the device 20 has been schematically separated into separate sections or "slices" to further clarify the specific dimensions and the multiplanar aspect of the device 20. In FIGS. 6A-6C, each slice 60A-60I is a cross-sectional section of the implant 20 that extends from the proximal side 22 to the distal side 24 such that each slice represents a section of the device 20 at a specific point along the length between the lateral side 26 and the medial side 28. FIG. 6A depicts a perspective view of the slices (or "sections") 60A-60H, while FIG. 6B is a side view of the sections 60A-60I (as viewed from the distal side of the device) and FIG. 6C is a front view of each of the sections 60A-60I (as viewed from the medial side toward the lateral side of the device). As clearly shown in the figures, each section 60A-60I has a unique height along the length of its contact surface 30, thereby resulting in the complex multiplanar nature of the contact surface 30 of the device 20 as a whole. In other words, the slices closer to the lateral side (slices 60A-60D) have a greater height than the slices closer to the medial side (slices 60F-60I). In fact, progressing from slice 60A toward slice 60I, each adjacent slice has a lesser height than the previous slice. Thus, slice 60A has a greater height than slice 60B, which has a greater height than slice 60C, etc. It is this change in height across the slices 60A-60I that results in the realignment ramp A as discussed in detail above.

In addition, FIG. 7 also shows the device 20 schematically separated into separate sections 62A-62E. In this instance, each slice 62A-62E is a cross-sectional section of the implant 20 that extends from the lateral side 26 to the medial side 28 such that each slice 62A-62E represents a section of the device 20 at a specific point along the length from the proximal side 22 to the distal side 24. More specifically, FIG. 7 depicts a perspective view of the sections 62A-62E. As can be easily seen from the figure, each section 62A-E has a unique height along the length of its contact surface 30, thereby adding to the complex multiplanar nature of the contact surface 30 of the device 20 as a whole. In other words, the slices closer to the proximal side (slices 62B and 62C) have a greater height than the slices closer to the distal side (slices 62D and 62E). In fact, progressing from slice 62B to slice 62E, each adjacent slice has a lesser height than the previous slice. Thus, slice 62B has a greater height than slice 62C, which has a greater height than slice 62D, etc. It is this change in height across the slices 62B-62E that results in the elevation ramp C as discussed in detail above. (It is noted that slice 62A actually has a lesser height than slice 62B. This relates to the implant body not having any sharp angles or surfaces that could damage the patellar tendon, as discussed elsewhere herein as well.)

Figure 8A:
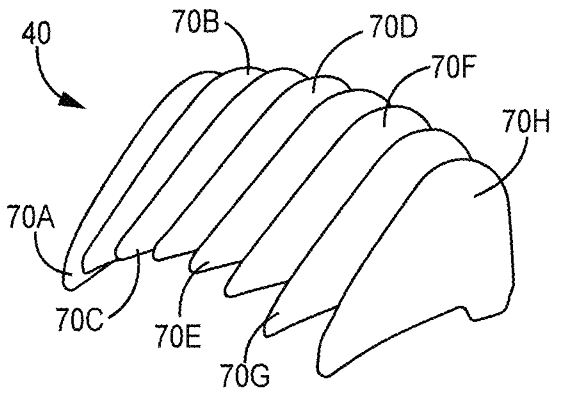
FIG. 8A PRIOR ART
FIG. 8A is a perspective view of schematic "slices" of a known "neutral" implant in which each slice is a cross-sectional section that extends from the proximal side to the distal side.
Figure 8B:
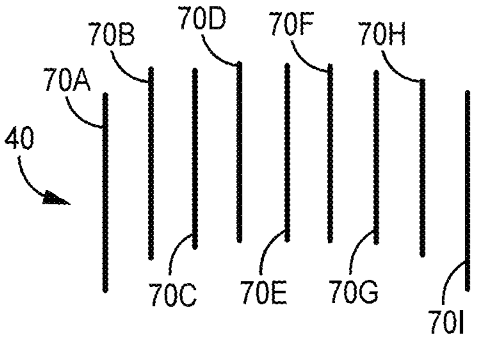
FIG. 8B PRIOR ART
FIG. 8B is a side view (from the distal side) of the slices of the known implant of FIG. 8A.
Figure 9:
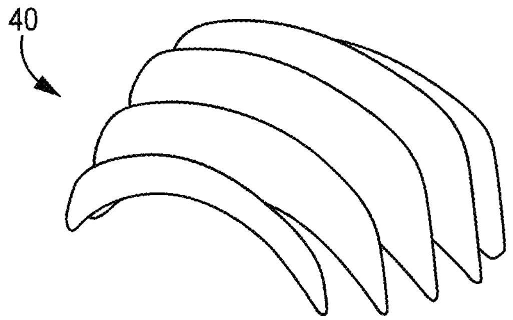
FIG. 9 PRIOR ART
FIG. 9 is a perspective view of schematic "slices" of a known "neutral" implant in which each slice is a cross-sectional section that extends from the lateral side to the medial side.
Figure 8C:
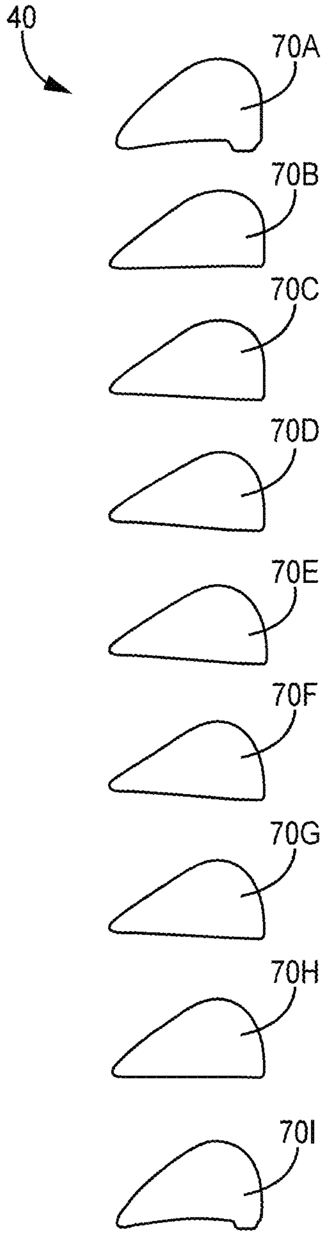
FIG. 8C PRIOR ART
FIG. 8C is a front view of each of the slices of the known implant of FIG. 8A.

In contrast, the known "neutral" device 40 is depicted in similar comparative detail in FIGS. 8A-9. As can readily be seen in those figures, each of the sections 70A-70I have the same or a substantially similar unique height along the length of its contact surface, thereby resulting in a contact surface that is only angled in one plane and thus does not have a complex multiplanar geometry.

While the various implant and method embodiments herein are discussed in the context of the device being implanted between the tibia and patellar tendon, it should be noted that the implant and method embodiments can also be used to treat other joints in the human body. For example, the various implementations herein can be used to treat issues with the shoulder (implanting the device between the superior glenoid and the rotator cuff or between the proximal humerus and the rotator cuff), the ankle (implanting the device between the Achilles tendon and the posterior calcaneus), the spine (implanting the device between facet joints), the hip (implanting the device between the pelvis and the gluteal muscles or between the greater trochanter and the gluteal tendons), or other aspects of the knee (implanting the device between the iliotibial band and the lateral distal femur). In other words, the various implant and method embodiments disclosed or contemplated herein are not limited to implantation between the patellar tendon and the tibia and can be used to unload other tendons and/or take pressure off other joints.

Figure 10A:
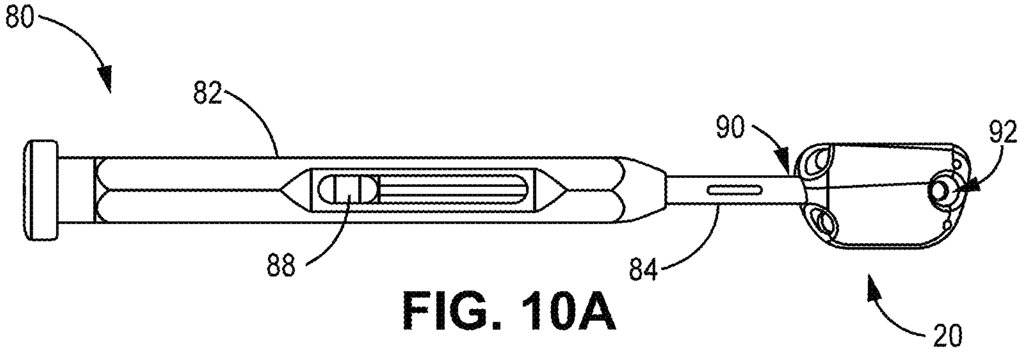
FIG. 10A is a side view of an implantation device, according to one embodiment.
Figure 10B:
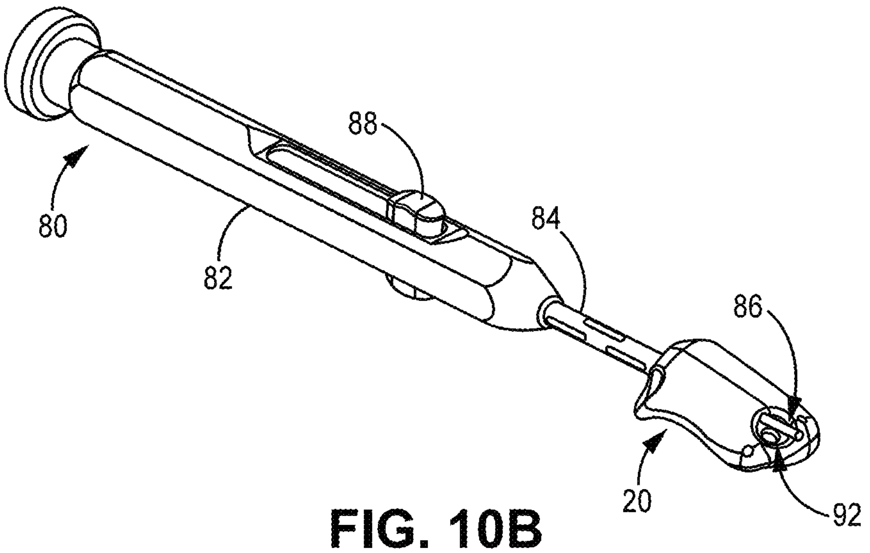
FIG. 10B is a perspective view of the implantation device of FIG. 10A, according to one embodiment.
Figure 11:
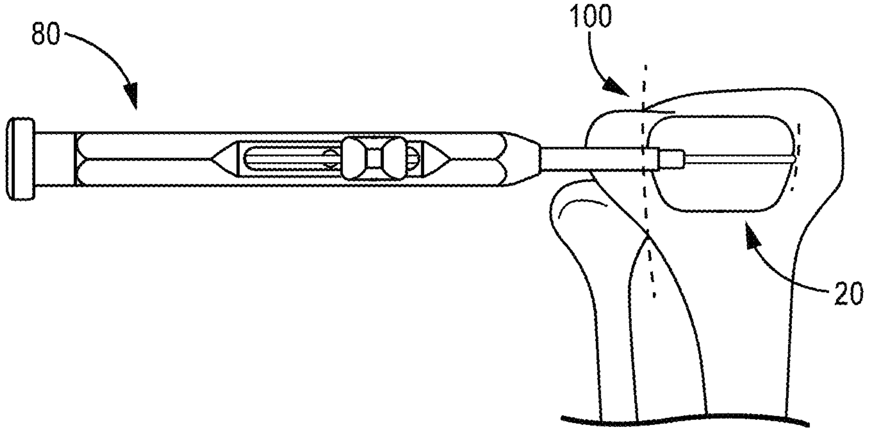
FIG. 11 is a side view of an implantation device being used to implant a multiplanar implant into a patient's knee, according to one embodiment.

According to certain implementations as shown in FIGS. 10A-11, an implantation device 80 can be used to position any of the implant embodiments herein between the tibia and the patellar tendon. The device 80 has an elongate handle 82 with a distal tube 84 extending from the handle 82 such that a deployable pin 86 can be slidably disposed through the tube 84. Further, the slidable pin 86 can have a button or other protrusion 88 attached to or extending from the pin 86 such that a surgeon can use the button 88 to urge the pin 86 between its deployed position (as shown in FIG. 10B) and its retracted position (as shown in FIG. 10A). In use, the distal end of the distal tube 84 can be attachable to an opening (or "port") 90 on the implant 20 such that the device 20 is attached to the tube 84. In example, the distal end of the tube 84 can have threads that are mateable with corresponding threads of the port 90. Alternatively, any known coupling structure, feature, or mechanism can be used. Further, once the implant 20 is attached to the implantation device 80, the slidable pin 86 can be urged into its deployed position such that the pin 86 extends through the implant 20 and out of another port 92 on the other side of the implant 20 as shown in FIG. 10B. As discussed in further detail below, the deployable pin 86 can be deployed during the procedure to serve as a locating device after the implant 20 has been positioned between the tibia and the patellar tendon.

Figure 16:
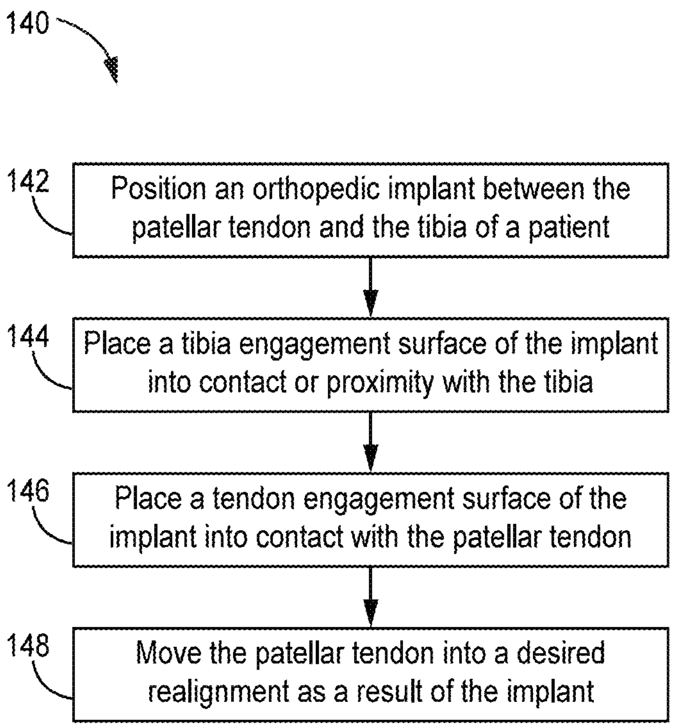
FIG. 16 is a flow chart of the steps of one method of using a multiplanar implant, according to one embodiment.

One specific implantation method will now be described, according to one exemplary embodiment with reference to FIG. 16. A set of implants (such as a selection of three implants, for example) for the appropriate knee (right or left) is provided such that the appropriate size can be selected depending on the specific anatomy of the patient. Further, in some alternative implementations, a set of trial implants that replicate the sizes of the available implants is also provided.

Figure 12:
FIG. 12 is a side view of a K-wire, according to one embodiment.
Figure 13:
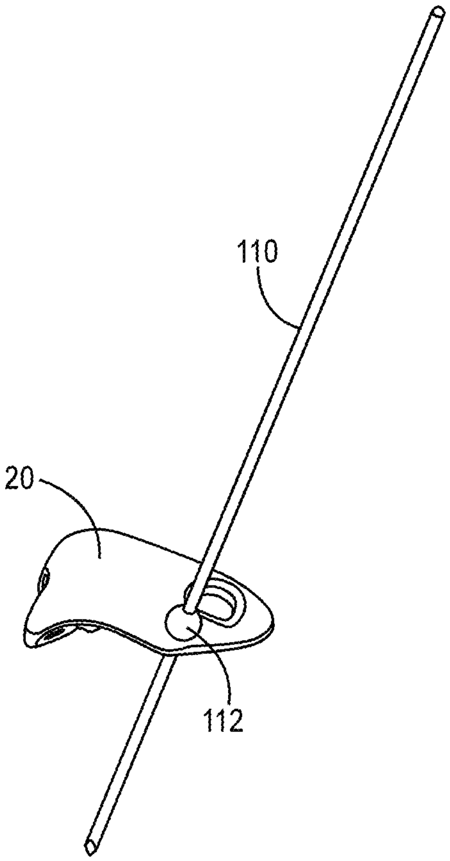
FIG. 13 is a perspective view of the K-wire of FIG. 12 being positioned through an opening in a multiplanar implant, according to one embodiment.

Once the appropriate devices and equipment are available, a first incision 100 is made on the lateral side of the patellar tendon of the right knee as shown schematically in FIG. 11. It is understood that a similar procedure on the left knee would be substantially the same, but using an appropriate left knee implant. In one embodiment, the incision 100 can be about 4 cm. Alternatively, the incision 100 can be any necessary length. Once the incision 100 is made and appropriate tissues are manipulated to provide sufficient access, in those embodiments in which a trial implant is used, a trial implant (not shown) of the desired size is inserted through the incision 100 and positioned between the patellar tendon and the tibia as shown in FIG. 11. Once the trial implant is disposed as desired, it can be secured with a K-wire, such as, for example, the K-wire 110 as shown in FIG. 12 such that the K-wire 110 can be positioned through an opening in the trial implant and into the tibia, thereby temporarily attaching the implant 20 thereto. The K-wire 110, according to certain embodiments, has a spherical stop 112 that is larger than any opening in the implant through which the K-wire 110 would be inserted (as shown in FIG. 13), thereby allowing the K-wire 110 to hold the implant in place. In certain implementations, the K-wire 110 can also have threads along the length of the K-wire at or near the distal end thereof.

Once the trial implant is attached, the fit of the implant can be assessed. In some implementations, an appropriately sized trial implant will seat anatomically beneath the patellar tendon without extending proximally above the tibial plateau. Further, the appropriate elevation slope of the trial implant will typically provide optimal lateral tendon elevation while ranging the knee without excessive prominence. In addition, the distal side of the trial implant should not apply pressure against the tendon insertion site. Further, optimal placement can be when the implant centerline is parallel to the tendon centerline and the lateral side of the implant is fully underneath & supporting the lateral edge of the tendon. Alternatively, any other factors or none of these factors may be considered. Once the fit has been confirmed visually (and in some cases with intraoperative fluoroscopy), the trial implant is removed.

Once the trial implant is removed, or in those embodiments in which a trial implant is not used, the next step is that the appropriately sized implant 20 is attached to the distal tube 84 of the implantation device 80 as shown in FIGS. 10A and 10B. The implant 20 is then positioned between the patellar tendon and the tibia of the patient (block 142). In a specific exemplary implementation, the implant 20 is inserted underneath the patellar tendon and positioned such that the lateral side of the implant 20 is aligned with the lateral edge of the tendon. That is, the lateral edge of the implant 20 should be aligned parallel and immediately beneath the lateral border of the patellar tendon. In this position, the tibia engagement surface of the implant is disposed in contact with or in proximity to the tibia (block 144), and the tendon engagement surface is in contact with the patellar tendon (block 146). Once the implant 20 is positioned as desired, the implant 20 can be temporarily fixed in place with a K-wire 110 in a fashion shown in FIG. 13. In one embodiment, the K-wire 110 is inserted through an opening on the medial side of the implant 20 as shown.

Figure 14A:
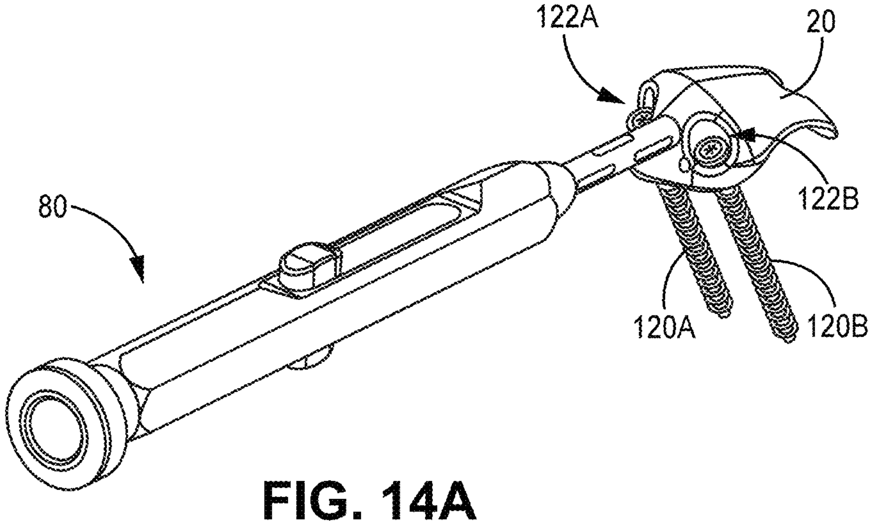
FIG. 14A is a perspective view of an implantation tool attached to a multiplanar implant with two fixation screws disposed through the implant, according to one embodiment.
Figure 14B:
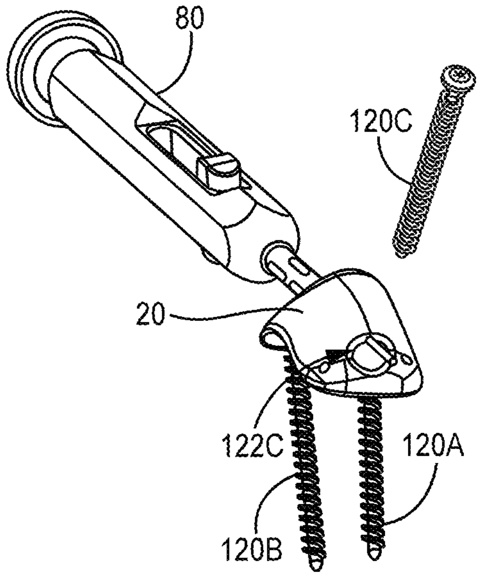
FIG. 14B is a different perspective view of the tool, implant, and two fixation screws of FIG. 14A with a third screw being positioned to be inserted through the implant as well, according to one embodiment.

Once the implant 20 is fixed in place with the K-wire 110, the implant 20 can be attached to the tibia via two fixation screws 120A, 120B being inserted through the two openings (or "screw holes") 122A, 122B in the lateral side of the implant as shown in FIG. 14A. Once the two screws 120A, 120B are screwed securely into place, the K-wire 110 can be removed and a third screw 120C can be inserted through the screw opening 122C on the medial side of the implant 20 as shown in FIG. 14B. FIG. 14C shows the implant 20 with all three screws 120A-C positioned through the implant 20 and embedded in the tibia (not shown).

According to one implementation, the positioning of the third screw 120C into the opening 122C on the medial side can be accomplished using the slidable locator pin 86 as discussed above. That is, the location of the medial screw hole 122C can be located by urging the slidable pin 86 into the deployed position such that the pin 86 extends out of the screw hole 122C (in a fashion similar to that depicted in FIG. 10B) such that the pin 86 can be seen or felt under the skin. As such, the distal end of the pin 86 visible or detectable under the skin indicates the location of the medial screw hole 122C such that the third fixation screw 120C can be properly positioned to insert it through the screw hole 122C despite the hole 122C not being visible (because it's under the skin).

Figure 15:
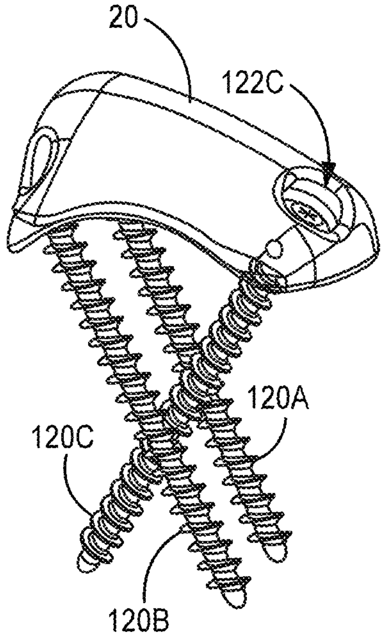
FIG. 15 is a perspective view of the implant of FIGS. 14A and 14B with all three fixation screws positioned therethrough, according to one embodiment.

Once the three screws 120A-C are firmly screwed into the tibia as shown in FIG. 15, the implantation device 80 can be removed by detaching the distal tip of the tube 84 from the implant 20. At this point, the placement of the implant 20 under the patellar tendon results in the tendon being moved into a desired realignment. For example, in one embodiment, the implant 20 can not only lift the tendon away from the tibia (thereby "unloading" the tendon), but also realign the tendon by urging the tendon medially or laterally, thereby repositioning the tendon in at least two planes as discussed in further detail above. In accordance with additional implementations, the implant can also cause the patellar tendon to rotate around its longitudinal axis, thereby resulting in a "tilting" of the tendon and creating a realignment in a third plane (the "axial plane"), as also discussed above. In yet other embodiments, this realignment of the patellar tendon can also result in realignment of the patella as well, which is discussed above as well. Once the implant 20 has been fixed in place and the tendon has been realigned as desired, the surgeon can evaluate the range of motion of the knee and tracking of the patellar tendon by flexing and extending the knee. Ideally, the realigned tendon should track directly over the implant with visible elevation of the lateral patellar tendon and no tendon subluxation. Further, in certain embodiments, the position of the implant and screws can be confirmed with intraoperative fluoroscopic imaging (including, for example, in either or both of the A/P and lateral views).

While the various systems described above are separate implementations, any of the individual components, mechanisms, or devices, and related features and functionality, within the various system embodiments described in detail above can be incorporated into any of the other system embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount—including any integer—between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾ This applies regardless of the breadth of the range. Although the various embodiments have been described with reference to preferred implementations, persons skilled in the art will recognize that changes may be made in form and detail without departing from the spirit and scope thereof.

Although the various embodiments have been described with reference to preferred implementations, persons skilled in the art will recognize that changes may be made in form and detail without departing from the spirit and scope thereof.

What is claimed is:

1. An orthopedic implant comprising:
- a) an implant body comprising a top side, a bottom side, a distal side, a proximal side, a medial side, and a lateral side;
- b) a bone contact surface disposed on the bottom side, the bone contact surface configured to be contactable with a bone; and
- c) a tendon contact surface disposed on the top side, the tendon contact surface comprising:
  - i) an elevation ramp sloping downward from the proximal side to the distal side of the implant body; and
  - ii) a realignment ramp sloping downward from the lateral side to the medial side of the implant body, wherein the tendon contact surface is configured to dynamically reposition a tendon movably disposed on the tendon contact surface by (a) rotating the tendon around its longitudinal axis, and (b) translating or shifting the tendon toward the medial side of the implant body along its horizontal plane, including during joint movement.

2. The orthopedic implant of claim 1, wherein the elevation ramp slopes downward from the proximal side to the distal side of the implant body at an angle of from 5 degrees to 35 degrees, wherein the angle of from 5 degrees to 35 degrees can have a variation from those amounts ranging from 0% to 10%.

3. The orthopedic implant of claim 1, wherein the realignment ramp slopes downward from the lateral side to the medial side of the implant body at an angle of from 5 degrees to 30 degrees, wherein the angle of from 5 degrees to 30 degrees can have a variation from those amounts ranging from 0% to 10%.

4. The orthopedic implant of claim 1, wherein the bone contact surface comprises at least two feet arranged to support the implant while attached to the bone.

5. The orthopedic implant of claim 1, wherein the bone contact surface comprises two feet arranged in cooperation with an articulating surface to support the implant while attached to the bone.

6. The orthopedic implant of claim 1, further comprising a fixation mechanism associated with the implant body, wherein the fixation mechanism is configured to attach the implant body to the bone.

7. The orthopedic implant of claim 6, wherein the fixation mechanism comprises:
- (a) at least two openings defined through the implant body; and
- (b) at least two fixation screws, wherein each of the at least fixation screws is configured to be positionable through one of the at least two openings.

8. The orthopedic implant of claim 1, wherein the bone is a tibia, and wherein the tendon is a patellar tendon.

9. An orthopedic implant comprising:
- a) an implant body comprising a top side, a bottom side, a distal side, a proximal side, a medial side, and a lateral side;
- b) a tibia contact surface disposed on the bottom side, the tibia contact surface configured to be contactable with a tibia; and
- c) a tendon contact surface disposed on the top side, the tendon contact surface comprising:
  - i) an elevation ramp sloping downward from the proximal side to the distal side of the implant body; and
  - ii) a realignment ramp sloping downward from the lateral side to the medial side of the implant body, wherein the implant body is configured to be implanted in a knee of a patient such that a patellar tendon is moveably disposed on the tendon contact surface such that the tendon contact surface is configured to dynamically change a position of the patellar tendon, including during flexing and extension of the knee, by (a) rotating the patellar tendon around its longitudinal axis, and (b) translating or shifting the patellar tendon toward the medial side of the implant body along its horizontal plane when the tibia contact surface is engaged with the tibia.

10. The orthopedic implant of claim 9, wherein the changing the position of the patellar tendon further results in tilting a patella coupled to the patellar tendon along its coronal plane.

11. The orthopedic implant of claim 9, wherein the elevation ramp slopes downward from the proximal side to the distal side of the implant body at an angle of from 5 degrees to 35 degrees, wherein the angle of from 5 degrees to 35 degrees can have a variation from those amounts ranging from 0% to 10%.

12. The orthopedic implant of claim 9, wherein the realignment ramp slopes downward from the lateral side to the medial side of the implant body at an angle of from 5 degrees to 30 degrees, wherein the angle of from 5 degrees to 30 degrees can have a variation from those amounts ranging from 0% to 10%.

13. The orthopedic implant of claim 9, wherein the tibia contact surface comprises two feet arranged in cooperation with an articulating surface to support the implant while attached to the tibia.

14. The orthopedic implant of claim 9, further comprising a fixation mechanism associated with the implant body, wherein the fixation mechanism is configured to attach the implant body to the tibia.

15. A method for repositioning a patellar tendon, the method comprising:

inserting an orthopedic implant having a tendon engagement surface between the patellar tendon of a knee and a tibia, wherein the tendon engagement surface comprises:
- a) an elevation ramp sloping downward from the proximal side to the distal side of the orthopedic implant; and
- b) a realignment ramp sloping downward from the lateral side to the medial side of the orthopedic implant;

engaging a tibia engagement surface of the orthopedic implant with the tibia;

engaging the patellar tendon with the tendon engagement surface such that the patellar tendon is moveably disposed on the tendon engagement surface; and causing a repositioning of the patellar tendon via the tendon engagement surface, including during knee movement, by (a) rotating the patellar tendon around its longitudinal axis, and (b) translating or shifting the patellar tendon toward the medial side of the orthopedic implant along its horizontal plane.

16. The method of claim 15, wherein the repositioning of the patellar tendon further causes tilting a patella coupled to the patellar tendon along its coronal plane.

17. The method of claim 15, wherein the step of engaging the tibia engagement surface further comprises adjusting the position of the implant for support by three projections positioned in a spaced apart arrangement on a bottom side of the implant.

18. The method of claim 16, wherein the three projections comprising two feet and an articulating surface.

19. The method of claim 15, further comprising attaching the orthopedic implant to the tibia after engaging the tibia engagement surface with the tibia.

* * * * *